United States Patent [19]

Clark

[11] Patent Number: 4,537,574
[45] Date of Patent: Aug. 27, 1985

[54] DENTAL ARTICULATOR

[76] Inventor: Alan D. Clark, 810 Gardendale, Ferndale, Mich. 48220

[21] Appl. No.: 478,243

[22] Filed: Mar. 24, 1983

[51] Int. Cl.³ .............................................. A61C 19/04
[52] U.S. Cl. ........................................ 433/69; 433/73
[58] Field of Search ....................... 433/55, 57, 58, 68, 433/69, 71, 73

[56] References Cited

U.S. PATENT DOCUMENTS

| | | | |
|---|---|---|---|
| 1,070,123 | 8/1913 | Evans . | |
| 2,070,025 | 2/1937 | Phillips | 32/32 |
| 2,180,673 | 11/1939 | Galetti | 32/32 |
| 2,418,648 | 4/1947 | Kile | 32/19 |
| 3,035,348 | 5/1962 | Page | 32/20 |
| 3,052,030 | 9/1962 | Spence | 32/32 |
| 3,074,166 | 1/1963 | Skallerup | 433/69 |
| 3,423,834 | 1/1969 | Irish | 433/67 |
| 3,431,649 | 3/1969 | Guichet | 32/20 |
| 3,452,439 | 7/1969 | Lee | 433/55 |
| 3,577,639 | 5/1971 | Lee | 32/19 |
| 4,126,938 | 11/1978 | Lee | 32/20 |
| 4,304,551 | 12/1981 | Kawasaki | 433/69 |
| 4,368,041 | 1/1983 | Roup | 433/69 |

*Primary Examiner*—Robert P. Swiatek
*Assistant Examiner*—Kris R. Schulze
*Attorney, Agent, or Firm*—Gifford, VanOphem, Sheridan, Sprinkle & Nabozny

[57] ABSTRACT

A method and apparatus for performing prosthodontic work comprises a face bow formed from a plate which supports impression styli which, when removed from the patient's head, is incorporated as the upper arm of the dental articulator. At least one, but preferably two, impression receptacles containing impressionable material are detachably secured to a lower face bow in registration with the stylus on the upper face bow to form the impression. Each receptacle is removed from the lower face bow after age hardening of the impression, and is secured to an articulator base at a position which maintains registration between the stylus and the impression formed in the receptacle. The impression formed thus forms a condylar guide hinge for mounting the upper arm of the articulator, preferably the upper face bow to the base, for simulating the condylar movement of a particular patient with respect to dental impressions to be used in forming dental prostheses to be worn by the patient.

14 Claims, 6 Drawing Figures

U.S. Patent  Aug. 27, 1985  Sheet 1 of 3  4,537,574
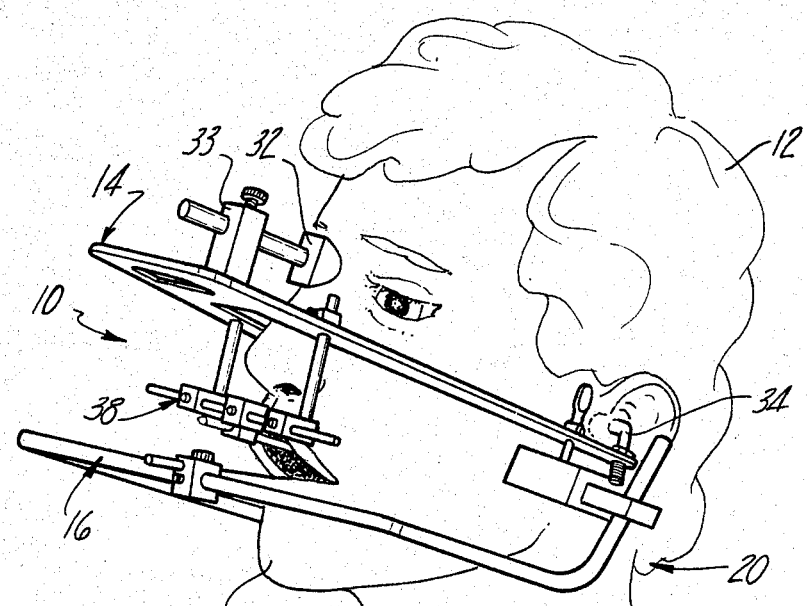
Fig-1
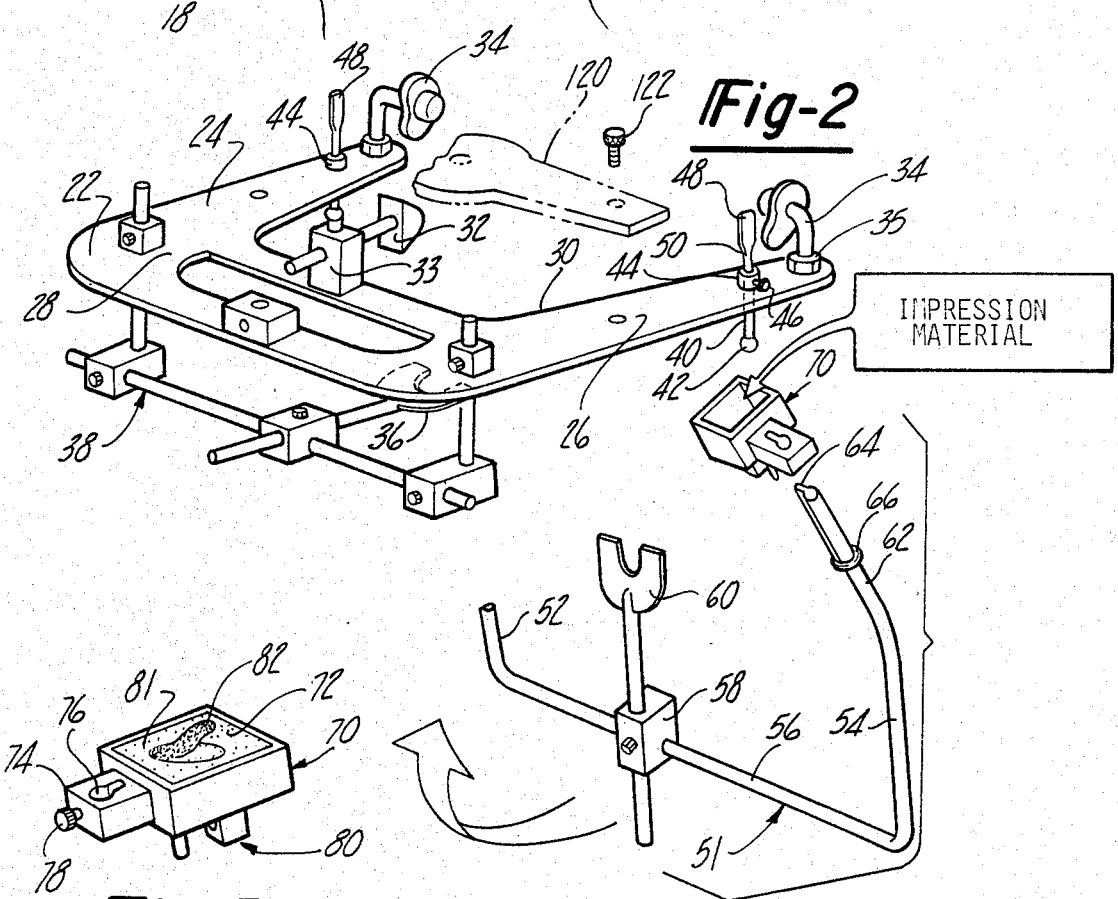
Fig-2
Fig-3

DENTAL ARTICULATOR

BACKGROUND OF THE INVENTION

1. Field of the Present Invention

The present invention relates generally to apparatus used in dentistry, and more particularly to a dental articulator for simulating the movement of upper and lower dental prostheses within the normal range of movement of a particular condylar construction.

2. Description of the Prior Art

A dental articulator is a form of jig employed in prosthodontics to assure that the dental prostheses are accurately configured to permit mating of the occlusal surfaces and unobstructed, comfortable displacement of the prostheses when secured to the jaw structures of the patient. Generally, the previously known articulators comprise an upper arm adapted to support an upper dental cast including prostheses which is slidably, displaceably secured to a base adapted to support a lower dental cast including prostheses. The means for displaceably securing the upper arm to the base generally comprises an adjustable displacement hinge mechanism which permits relative movement between the arm and the base, and thus between the dental casts, to approximately simulate relative movement between the upper and lower prostheses which would normally occur in the mouth by means of the condylar joint connecting the mandible to the maxillary structure of the patient's head. Typically, the inclination of the displacement in the hinge means is adjustable so that actual differences between various condylar structures can be approximately replicated by a single articulator. One of these previously known articulators is disclosed in U.S. Pat. No. 4,304,551 to Kowasaki.

The disadvantage of the previously known articulators is that the hinge means, or condylar guidance mechanism, provides movement which is similar to, but not accurately representative of, the movement caused by an individual's condylar joint. Thus, while the articulators are of some benefit in aligning and fitting dental casts so that displacement along their occlusal surfaces occurs without obstruction, substantial work may still be necessary upon the prostheses once they are installed in the patient's mouth to accomodate the actual movement caused by the patient's condylar joint. Moreover, the articulators are complex structures and due to the complexity of the parts, especially the condylar guidance hinge, are therefore quite expensive to produce and purchase.

One previously known method for increasing the accuracy of simulated condylar movement of the dental impression is to record a graph of the actual movement produced by a patient's condylar movement and aligning the condylar hinge of the articulator in accordance with the graph record produced. Nevertheless, once the general slope of condylar movement has been determined, the articulator only approximates actual movement since the line of displacement in the articulator, such as the articulator disclosed in U.S. Pat. No. 4,304,551, is restricted to a linear displacement regardless of the actual, varying slope to which movement is adjusted.

Moreover, the making of the graph is a rather complicated procedure. A writing stylus is secured to an upper face bow, a frame structure adapted to be fixedly secured to the maxillary structure of a patient's head. A graph plate upon which the stylus writes is secured to a lower face bow, a frame structure adapted to be fixedly secured to the mandibular structure of the patient. The stylus and graph plate are positioned so as to be in registration with one another so that movement of the mandible with respect to the maxillary structure permits the stylus to imprint a graphic representation of the movement on the graph plate. Such structure is also rather complex and expensive due to the mechanisms which are necessary to securely fit the face bow to the patient.

Another previously known improvement which permits the articulator to more closely simulate the actual movement of a particular condylar structure comprises a use of an impression stylus fixedly secured with respect to the maxillary structure, which forms an impression in impressionable material fixed with respect to the mandibular structure. Such an impression forms a more accurate record of the movement of the patient's jaw. Such impressions can be formed within the oral cavity, or exteriorly of the oral cavity, but in either case, it is typically formed at a position away from the condylar axis so that the impression, or a cam guide surface formed from the impression, can be mounted on the previously known articulator. The impression, or cam guide surface, is then used to control the operation of the condylar hinge means of the articulator for example, by means of an incisal pin which rides in the cam guide surface, and operates in conjunction with the condylar hinge means.

Nevertheless, the complex and time consuming procedure of forming the impression is quite similar to the procedure outlined above with respect to the graphic recording of condylar joint movement. Moreover, incorporation of the impression in the articulator further increases the cost and complexity of the dental articulator. Moreover, even though the condylar hinge means can be made mechanically responsive to the guiding surface of the impression material incorporated in the articulator, maladjustment of the hinge means or limitations in its range of movement can interfere with accurate displacement of the upper and lower dental impressions despite the accuracy of the movement impression made during the actual movement of the patient's jaw.

SUMMARY OF THE PRESENT INVENTION

The present invention overcomes the above-mentioned disadvantages by providing a method and apparatus for accurately reproducing the displacement of a particular condylar joint in an articulator by incorporating an impression formed during movement of the jaw into the articulator as the condylar hinge means. The present invention avoids the need for previously known, complex condylar hinge means for connecting the upper arm of the articulator to the base of the articulator. In addition, the present invention avoids the need for a separate upper arm structure on the articulator by permitting the upper face bow to be incorporated with the base of the articulator to form the complete articulator. As a result, the method and apparatus of the present invention are substantially less complex and less expensive than previously known procedures and apparatus used in prosthodontics.

In general, the movement impression is made by mounting upper and lower face bows to the face of the patient. Preferably the face bow is in the form of a U-shaped plate to fit around the head of the patient, and includes means for fixedly positioning the plate with respect to the head of the patient. Preferably, the positioning means of the face bow includes an adjustable nasion holder, adjustable ear plugs, and an adjustable dental clutch adapted to mate with the upper dental surface of the patient. The face bow also includes a stylus on each side positioned near and adjacent to the condylar joint of the patient. A lower face bow, preferably a substantially U-shaped rod with inclined portions at the ends of its parallel arms includes means for fixedly positioning the face bow to the mandible of the patient. Preferably, this positioning means comprises a lower dental clutch adapted to mate with the lower dental structure. The inclined ends of the arms of the lower face bow include means for removably securing a receptacle adapted to receive the stylus therein in communication with a supply of impressionable material in the receptacle.

Once the face bows have been mounted to the patient, the receptacle is filled with impressionable material, preferably an age hardening material which communicates with the stylus so that movement of the stylus during movement of the patient's jaw forms an impression in the impressionable material.

Once the impression has been made and permitted to harden, the receptacle is removed from the lower face bow and secured to the base of the articulator of the present invention. The base includes a means for supporting the receptacles in a spaced apart relationship substantially identical to the relationship of the receptacles when mounted on the lower face bow. When the upper face bow is removed from the patient, the styli remains secured to the face bow. The styli are thus positioned to be received within the receptacles within the impression formed in the material contained in the receptacle. A means for mounting the upper dental cast is then secured to the face bow plate so that the face bow becomes the upper arm of the articulator. The mounting means can then be removed from the U-shaped plate. Of course, the base is also provided with means for supporting the lower dental cast in registration with the upper dental cast supported by the face bow plate. Thus, as the stylus is moved within the impression supported on the base of the articulator, the movement between the upper and lower dental impressions closely simulates the movement of the prostheses which would occur in the patient's mouth. Thus, the prostheses can be accurately configured to provide unobstructed and comfortable movement within the patient's mouth before the prostheses is mounted within the patient's mouth.

The present invention substantially reduces the cost of an articulator for accurately displacing dental structure cast as would occur in a patient's mouth. Moreover, in addition to the reduction in cost and complexity of the apparatus itself, the apparatus is simple to operate and set up for checking the movement between dental casts. Moreover, since the hinge forming impression can be formed at a position juxtaposed to the actual condylar joint, the impression formed is unaffected by irregularities in the mouth or jaw structure which can effect the impressions formed in or out of the mouth at other locations. As a result, the present invention provides many advantages over previously known dental articulators used in the reproduction of dental movement controlled by the condylar structure of the patient.

BRIEF DESCRIPTION OF THE DRAWINGS

The present invention will be more clearly understood by reference to the following detailed description of a preferred embodiment of the present invention when read in conjunction with the accompanying drawings in which like reference characters refer to like parts throughout the several views and in which:

FIG. 1 is a perspective view of apparatus for forming the condylar joint movement impression according to the present invention.

FIG. 2 is an enlarged perspective view of the apparatus shown in FIG. 1.

FIG. 3 is an enlarged perspective view of a portion of the device shown in FIGS. 1 and 2.

DETAILED DESCRIPTION OF THE PREFERRED EMBODIMENT OF THE PRESENT INVENTION

Figure 4:
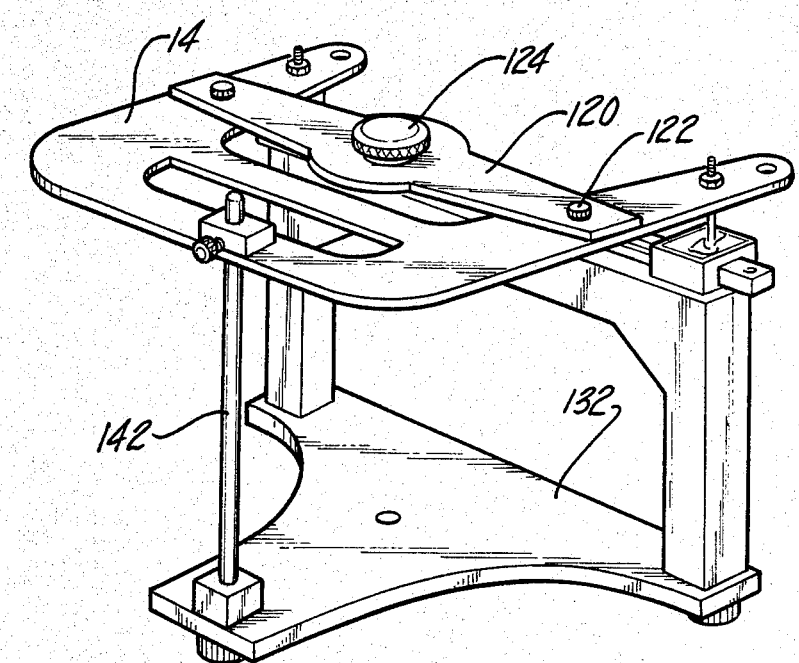
FIG. 4 is a perspective view of the dental articulator in accordance with the present invention.

Referring first to FIG. 1, a mechanism 10 for forming an impression of condylar movement is thereshown secured to the head 12 of a patient. The device 10 generally comprises an upper face bow 14 having means for fixedly positioning the face bow 14 with respect to the head 12 of the patient, and a lower face bow 16 including means for fixedly securing the face bow 16 to the mandibular structure 18 of the patient. The face bows include means, generally designated at 20 in FIG. 1, for recording displacement of the mandibular structure 18 with respect to the maxillary structure of the patient's head 12, and located substantially adjacent to the condylar structure of the head 12.

As best shown in FIG. 2, the upper face bow 14 comprises a flat, substantially U-shaped plate 22 having arms 24 and 26 extending rearwardly from an anterior bar or base portion 28 so as to form a recess 30 which receives the head 12 of the patient. The means for mounting the face bow 14 to a maxillary structure of the head include a nasion holder 32 adjustably secured by a toggle 33 at the center of the plate 28, and a pair of ear plugs 34 secured at the end of the arms 24 and 26 by adjustable means 35. In addition, face bow 14 includes a bite fork 36 adapted to be locked in registration with the occlusal surface of the maxillary dental structure by means of a toggle mechanism 38 which permits the bite fork 36 to be adjusted in three directions with respect to the plate 22 from the front or base end of the plate 22.

The plate 22 also includes means for mounting a pair of impression styli 40 to the plate 22 so that the impression forming end 42 of each stylus 40 extends adjacent the condylar joint in the head 12 of the patient. Preferably, the stem of each stylus 40 extends through a slot in one of the arms 24 and 26 in which a collar 44 can be lockingly engaged. In addition, the collar 44 includes a transverse threaded bore adapted to receive a thumb screw 46 so that the stem of the stylus 40 can be locked in the collar 44. Preferably, the stylus 40 includes an enlarged diameter stem portion 48 which provides an abutment surface 50 on the stem so that the ball-shaped impression end 42 is locked to the upper face bow at a predetermined distance with respect to the plate 22.

The lower face bow 16 comprises an elongated bar 51 formed in a substantially U-shaped, whereby shanks 52 and 54 extend rearwardly of the base bar portion 56. The base bar portion 56 supports a toggle mechanism 58 for positioning a bite fork 60 in three dimensions intermediate the shanks 52 and 54 to register with the mandibular dental structure. Each shank 52 and 54 includes an inclined end portion 62 having an elongated key 64 and an abutment rib 66 for positioning an impression receptacle housing 70 thereon.

As best shown in FIGS. 2 and 3, the receptacle housing 70 defines an open-topped impression chamber 72. A locking flange extending laterally outwardly from the peripheral wall of the chamber 72 includes a keyslot 76 adapted to receive the keyed shank ends 66 of the lower face bow bar 51. Thumb screw 78 threadably engages a transverse bore communicating with the keyhole slot 76 to permit the receptacle housing 70 to be locked on to the end 66 of the lower face bow 16. In addition, the bottom of receptacle housing 70 includes means, generally designated at 80 in FIG. 3, for mounting the receptacle housing 70 to an articulator base as will be described in more detail hereinafter.

Having thus described the important structures necessary to form a condylar movement impression adjacent the condylar structure of the patient, the operation of the structure is readily described. The upper face bow 14 and the lower face bow 16 are fixedly positioned to the maxillary structure and mandibular structure, respectively, of the patient's head 12, in a well known manner by adjustment of the nasion 32, the ear plugs 34 and the bite plates 36 and 60. The stylus 40 is lifted to the position shown in FIG. 2 so that the abutment surface 50 is raised above the locking collar 44. The chamber 72 in receptacle housing 70 can then be filled with an impressionable material 81, preferably an age hardening impressionable material of known composition. The stylus 40 is then lowered into the impressionable material within the chamber 72 until the abutment surface 50 rests against the collar 44. Stylus 40 is then locked into position by tightening the thumb screws 46 into abutment with the stem of the stylus 40. The impression forming end 42 of the stylus 40 thus displaces the impressionable material within chamber 72 as the patient's mandible is moved with respect to the maxillary structure. Preferably, the movement is controlled and limited to movement within the occlusal plane so that it moves both forwardly and rearwardly as well as side to side, causing the stylus to make an appropriate impression 82 in the impressionable material 81 contained in the chamber 72.

Figure 5:
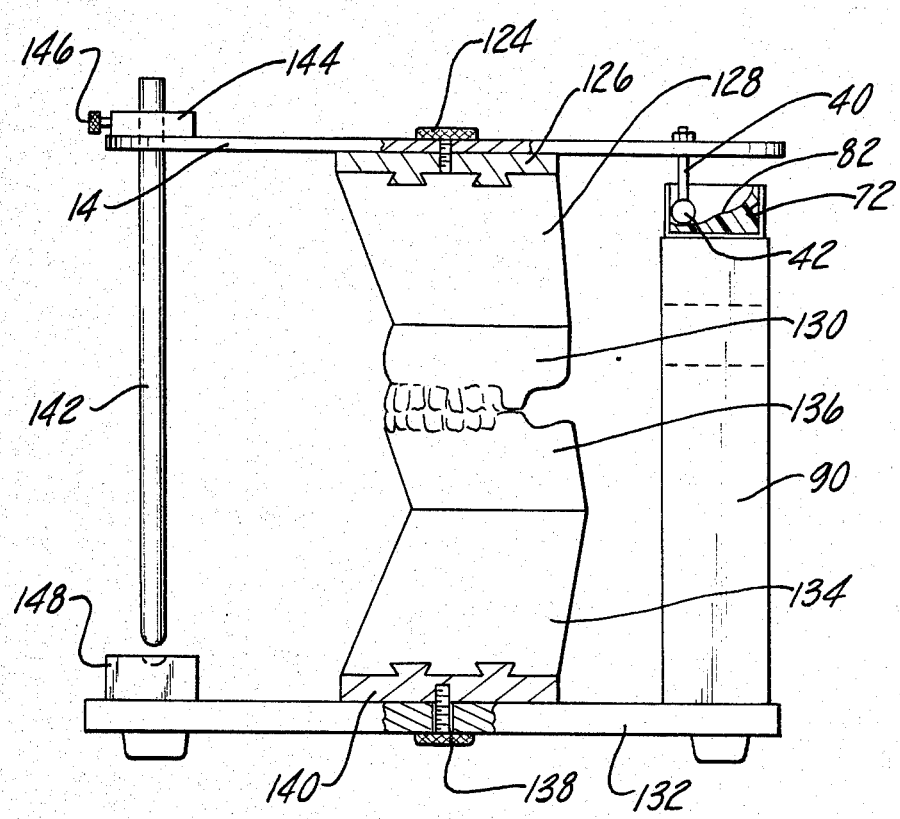
FIG. 5 is a sectional elevation of the articulator shown in FIG. 4.
Figure 6:
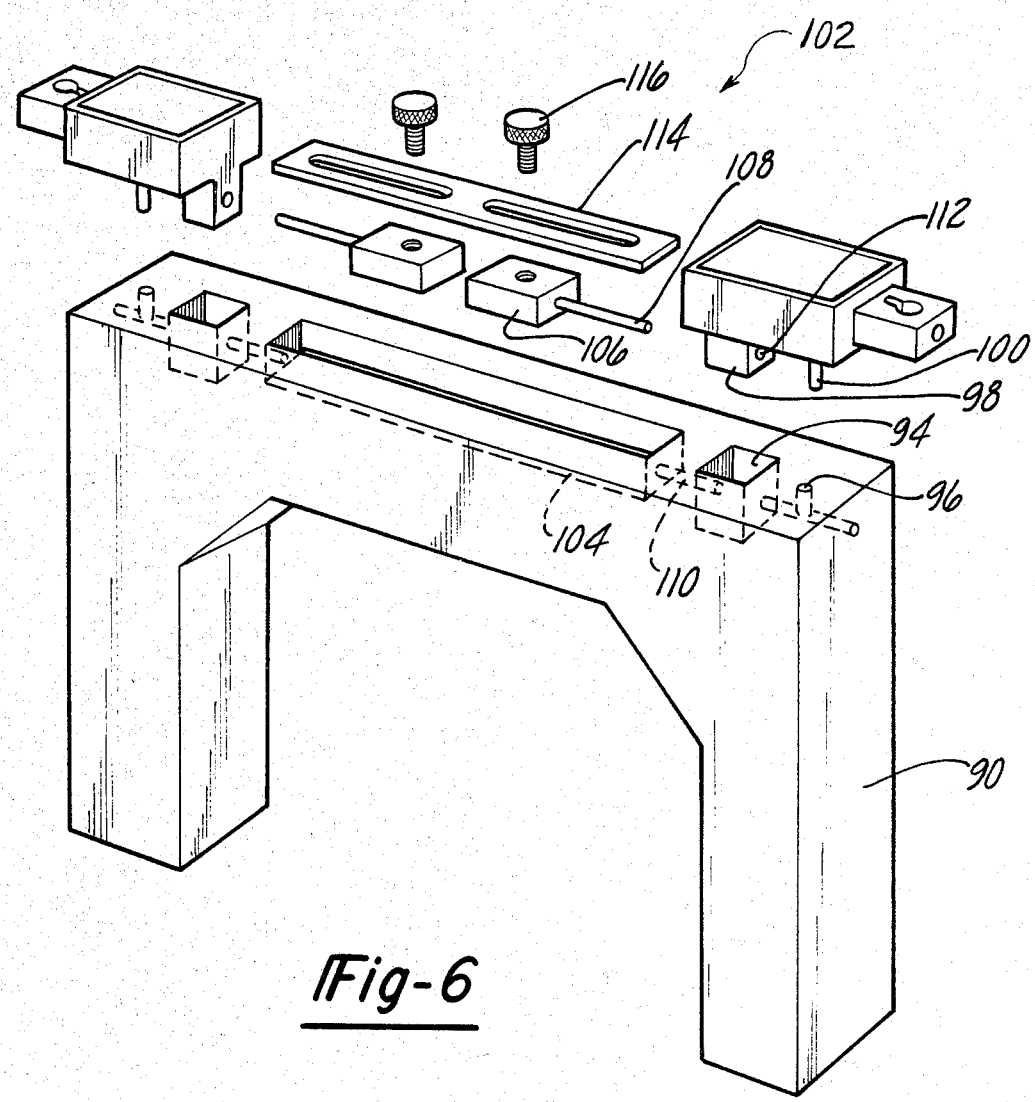
FIG. 6 is an enlarged perspective view of a portion of the device shown in FIGS. 4 and 6.

Referring now to FIGS. 4 through 6, receptacle housing 70 is removed from the lower face bow 14 and installed on an articulator base support member 90. As best shown in FIG. 6, the base support member 90 comprises a substantially arch-shaped stanchion having an apertured upper surface 92 with apertures 94 and 96 adapted to receive projections 98 and 100 extending from the bottom of the receptacle housing 70. The apertures 94 and 96 are spaced apart from the apertures 94 and 96 at the opposite end of the base support member 90 so that the chambers 72 of the receptacle housing 70 are spaced apart substantially the same distance by which they were separated when mounted to the lower face bow. Although two spaced apart projections 98 and 100 are shown in order to prevent rotation of the receptacle 70 when positioned on the base support member 90, it will also be understood that a single projection, such as the projection 98 shown in FIG. 6, can be configured with, for example, a square cross-section as shown, to prevent rotation of the receptacle while it remains mounted on the base support member 90.

The base support member 90 also includes a locking means 102 for locking the receptacle housings 72 on the base support member 90. As best shown in FIG. 6, a central elongated recess 104 is disposed intermediate the apertures 94 and is adapted to receive a pair of sliding blocks 106 therein. Each of the sliding blocks 106 includes an elongated locking pin 108 extending outwardly towards recess 94 through bore 110 in the upper portion of the base support member 90. In addition, the projection 98 on each receptacle housing 70 includes an aperture 112 adapted to register with the bore 110 when the receptacle housing 70 is positioned on the base support member 90. A locking plate 114 is secured to the base support member 90 over the sliding blocks 106 so as to slidably entrain the blocks 106 within the recess 104. Screw threaded block handles 116 extend through elongated slots in a retention plate 114 so that the locking blocks 106 can be manually slid into and out of engagement with the bores 110 and 112 in the support member 90 and receptacle housing 70, respectively.

Referring back to FIG. 4, and with receptacle housing 70 locked into position as previously discussed, the upper face bow 14 can be joined to the articulator base to form the upper arm of the articulator. Of course, the nasion holder 32 and its toggle 33, the adjustable ear plugs 34 and the bite plate 36 have been removed from the face bow 14. In addition, a cast support bracket 120 is secured across the recess 30 between the arms 24 and 26 of the plate 22 to provide a means for mounting a dental cast on the upper arm of the articulator. As best shown in FIG. 5, a thumb screw 124 extends through an aperture in support bracket 120 and threadably engages a cast support plate 126 integrally secured to a cast and luting structure 128. The cast structure 128 includes an upper dental formation 130 which is supported in a position corresponding to the position occupied by the patient's maxillary structure when the face bow 14 was secured to the head of the patient as shown in FIG. 1.

The base support member 90 is locked onto a base plate 132 with means for supporting a lower cast structure 134. The lower plaster cast and luting structure 134 includes a lower dental cast 136 mounted for registration with the upper dental cast 130. The supporting means comprises a thumb screw 138 extending through an aperture in the base plate 132 and threadably engaging an aperture in support plate 140 integrally connected to the cast support 134. The articulator also includes an incisal pin 142 adjustably secured to the face bow 14 by collar 144 mounted to leg 28 of the plate 22. The collar includes a transverse thumb screw 146 to lock the incisal pin 142 within the collar 144, so that when the incisal pin 142 rests against the stop block 148 or other anterior guidance means mounted on base plate 132, the face bow 14 is maintained at a height which permits the dental cast 130 and dental cast 136 to be maintained at a position simulating the closed position of prostheses which would naturally occur in the patient's mouth. In this position, it would be noted that the stylus 40 is positioned in the lowermost portion of the impression 82 at the forward end of the receptacle chamber 72. Mandibular movement can be simulated by moving the face bow 14 so that the stylus head 42 traces the impression 82 in the receptacle chamber 72, whereby the dental casts 130 and 136 are displaced in a manner which represents the actual movement of the patient's jaw. Accordingly, the casts and the prostheses included therein can be modified to provide unobstructed occlusal movement. Thus, the prostheses can be accurately constructed before the prostheses are installed within the mouth of the patient.

The present invention provides a simple and less expensive articulator by utilizing the face bow structure, previously used in recording condylar movement of the patient, in the articulator. In addition, the present invention provides a simple and inexpensive, condylar-type hinge for connecting the upper arm of the articulator to the base of the articulator by utilizing impressions formed during condylar movement. In addition, since the impressionable material can be positioned adjacent the condylar joint of the patient, the resulting impression more accurately conforms to actual movement of the condylar joint, and avoids the mechanical discrepencies in movement between upper and lower dental impressions which can be introduced by a previously known mechanical condylar hinge mechanisms. Moreover, the present invention provides a simpler method of forming the condylar movement impression than previously known devices.

In addition, the present invention simplifies the procedure for incorporating the casts in a dental articulator and avoids the need for complex condylar alignment adjustments of previously known condylar guide hinges of previous articulators. As a result, the method defined by the present invention is also simpler and less time consuming than previously known prosthodontic methods. In addition, the structure is substantially less complex and less expensive than previously known dental articulators, especially since the upper face bow also serves as an articulator arm.

Having thus described my invention, many modifications thereto will become apparent to those skilled in the art to which it pertains without departing from the scope and spirit of the present invention as defined in the appended claims.

What is claimed is:

1. A method for making a dental articulator having an upper arm adapted to support a maxillary dental cast, a base adapted to support a mandibular dental cast and hinge means for displaceably securing said arm to said base, said method comprising:
    applying a one-piece upper face bow having an anterior bar and a pair of spaced rearwardly extending arms to the head of a patient and fixedly positioning said upper face bow with respect to the maxillary dental structure of the patient,
    applying a lower face bow to the head of a patient and fixedly positioning said lower face bow with respect to the mandibular dental structure of the patient,
    fixedly vertically positioning and securing at least one impression stylus to one of said upper and lower face bows in a vertical alignment,
    fixedly positioning at least one impressionable material to the other of said upper and lower face bows at a corresponding position in which each said at least one stylus communicates with one said impressionable material,
    displacing said mandibular dental structure in an unconstrained manner with respect to said maxillary dental structure, whereby said stylus forms an impression in said impressionable material,
    incorporating said stylus and said impression in said articulator so that said each of said at least one stylus rides in each said one impression to form the sole condylar guide means for displaceably connecting said arm to said base,
    wherein said incorporating step further comprises:
    removing said upper face bow from the head of said patient, and
    mounting said upper face bow on said articulator base by placing said at least one stylus in said impressionable material whereby said upper face bow forms said upper arm of said articulator.

2. The invention as defined in claim 1, wherein said step of fixedly positioning said at least one impressionable material comprises filling a receptacle with age hardening material and removably securing said receptacle to said lower face bow, and
    intermediate said displacing step and said incorporating step, allowing said impression in said impressionable material to age harden.

3. The invention as defined in claim 2, wherein said at least one stylus is secured to said upper face bow, and further comprising mounting said impressionable material on said base, mounting said upper face bow, including said stylus, on said articulator base, by engaging said stylus in said impression, whereby said face bow forms said upper arm of said articulator.

4. The invention as defined in claim 3, and further comprising the step of removing said receptacle from said lower face bow, and
    mounting said receptacle to said base so that said receptacle is disposed in the same position relative to said at least one stylus as when mounted on said lower face bow.

5. The invention as defined in claim 1, wherein said steps of fixedly positioning said at least one stylus and said at least one impressionable material comprise juxtapositioning said stylus and said impressionable material laterally adjacent the condyles of the head structure of the patient.

6. The invention as defined in claim 1, wherein said at least one stylus comprises two styli, one stylus being fixedly positioned on each opposing side of said one face bow adjacent the condyles of the head of the patient, and wherein said at least one impressionable material comprises two portions of impressionable material each portion removably but fixedly secured to opposite sides of said lower face bow so as to communicate with the stylus on that side, whereby said steps of displacing and incorporating pertain to each stylus and its respective material portion.

7. A dental articulator for simulating the occlusal displacement of a particular condylar structure, said displacement being recorded by no more than two styli secured with respect to the maxillary structure of a patient, and receptacles corresponding in number with the number of styli; each receptacle being filled with impressionable material, fixed with respect to the mandibular structure of a patient and positioned in communication with a stylus so that said displacement records an impression by a stylus in each said receptacle's material, said articulator comprising,
    a one-piece face bow having an anterior bar and a pair of spaced rearwardly extending arms, means for detachably securing said face bow in a fixed position with respect to the maxillary structure of the patient and means for supporting at least one stylus,
    a base having means for receiving each said receptacle in a fixed position at which said receptacle is aligned in the same position with respect to respective stylus as during communication when displacement is being recorded, and means for detachably mounting the at least one receptacle in registration with the at least one stylus to form the sole condylar guidance means for said articulator at said fixed position, wherein said means for detachably mounting comprises means for locking each said receptacle to said base only when said receptacle is seated on said base in said fixed position, wherein each said receptacle includes an aperture, and wherein said means for locking comprises a pin adapted to be received in said aperture and means carried by said base for slidably displacing said pin longitudinally along said base into and out of said aperture when said aperture is aligned in registration with said pin, wherein said aperture is aligned with said pin only when said receptacle is seated on said base in said fixed position.

8. The invention as defined in claim 7, and further comprising means for mounting a dental cast, said mounting means extending across the rear arms of said face bow.

9. The invention as defined in claim 7 wherein said receptacle includes a depending projection and wherein said aperture comprises a bore formed in said projection and wherein said base includes a recess adapted to receive said projection.

10. The invention as defined in claim 9 wherein said projection includes means for inhibiting rotation of said projection in said recess.

11. An articulator for simulating occlusal displacement of a particular condylar structure, said displacement being recorded by at least one stylus, each of said at least one stylus being fixedly secured with respect to the maxillary structure of the head of a patient, receptacles corresponding in number to the number of styli, each receptacle being filled with impressionable material, fixed with respect to the mandibular structure of the patient and positioned so as to be in communication with one of said styli so that displacement of each said at least one stylus records an impression by said stylus in said material, the articulator comprising;

an upper arm formed by a one-piece face bow having an anterior bar and means for receiving an incisal pin and spaced apart, rearwardly extending arms, means for supporting an upper dental cast on said upper arm, a base having means for supporting a lower dental cast, and means for displaceably mounting said arm to said base comprising said at least one stylus, said at least one receptacle, and means for supporting said at least one receptacle in registration with said at least one stylus, whereby said stylus rides in said impression and wherein said stylus and impression form the sole condylar guidance means for controlling displacement of said upper arm with respect to said base, and wherein said means for supporting an upper dental cast comprises a bracket secured to and extending across said arms having means for mounting a dental cast.

12. The invention as defined in claim 11, wherein said at least one stylus comprises two styli and said at least one receptacle comprises two receptacles, and further comprising, an upper cast conforming to the patient's upper dental structure secured to said upper arm, a lower dental cast conforming to the patient's lower dental structure secured to said base, and means for mating the occlusal surfaces of said casts and wherein said means for displaceably mounting said receptacles comprises means for positioning said receptacles at a position conforming to the relative position of the condylar joint of the patient with respect to the patient's mating occlusal surfaces.

13. The invention as defined in claim 11 wherein said upper face bow is formed from a flat plate.

14. The invention as defined in claim 11 wherein said bracket is formed from a flat plate.

* * * * *